(12) United States Patent
Hsiao et al.

(10) Patent No.: US 9,279,799 B2
(45) Date of Patent: Mar. 8, 2016

(54) METHODS OF IMPROVING AUTO-CODING CAPABILITIES FOR BIOSENSORS AND DEVICES FOR SAME

(75) Inventors: Tsung-Sung Hsiao, New Taipei (TW); Wen-Huang Chen, Hsin-chu (TW); Keng-Hao Chang, Taichung (TW); Han-Ching Tsai, New Taipei (TW)

(73) Assignee: Tyson Bioresearch, Inc., Chu-Nan (TW)

( * ) Notice: Subject to any disclaimer, the term of this patent is extended or adjusted under 35 U.S.C. 154(b) by 1150 days.

(21) Appl. No.: 13/295,099

(22) Filed: Nov. 14, 2011

(65) Prior Publication Data
US 2013/0122532 A1 May 16, 2013

(51) Int. Cl.
*G01N 33/00* (2006.01)
*G01N 33/487* (2006.01)

(52) U.S. Cl.
CPC . *G01N 33/48771* (2013.01); *Y10T 436/144444* (2015.01)

(58) Field of Classification Search
CPC ................................................ G01N 33/48771
See application file for complete search history.

(56) References Cited

U.S. PATENT DOCUMENTS

| | | |
|---|---|---|
| 2006/0144704 A1 | 7/2006 | Ghesquiere et al. |
| 2007/0015286 A1 | 1/2007 | Neel et al. |
| 2007/0110615 A1* | 5/2007 | Neel ................ G01N 33/48771 422/400 |
| 2008/0229850 A1 | 9/2008 | Huang et al. |
| 2009/0125268 A1 | 5/2009 | Perry |
| 2010/0255567 A1 | 10/2010 | Lieber et al. |
| 2010/0288841 A1 | 11/2010 | Ripley et al. |

* cited by examiner

*Primary Examiner* — Sam P Siefke
(74) *Attorney, Agent, or Firm* — Eastwind Consultants Co., Ltd.; Jenny Chen

(57) ABSTRACT

The present invention discloses a biological measuring device with auto coding capabilities. In accordance with one embodiment of the present invention, the biological measuring device with auto coding capabilities may include a test strip associated with a code pattern; and a code reader electrically coupled to the test strip to read the code pattern, wherein the code reader is configured to read an output from the code pattern consisted of a first logical value, a second logical value, and a third logical value.

9 Claims, 4 Drawing Sheets

METHODS OF IMPROVING AUTO-CODING CAPABILITIES FOR BIOSENSORS AND DEVICES FOR SAME

FIELD OF THE INVENTION

The present invention relates to biosensors and test strips for same; in particular, the present invention relates to methods of improving auto-coding capabilities for biosensors and devices for same.

BACKGROUND OF THE INVENTION

Electrochemical measuring devices have been commonly used to determine the concentration of analytes in body fluids. For example, in blood-glucose testing, a blood sample may be dropped at a measuring end of a test strip that is applied with an enzyme, and then the test strip may be inserted into a glucose meter to determine the concentration of glucose in the blood sample.

In the conventional art, the test strip is provided with a working electrode and a reference electrode to form a reaction region. The reaction region is applied with the enzyme so that when a test sample reacts with the enzyme, a chemical response is generated. When in use, the test strip is inserted in the glucose meter so that the glucose meter can read the chemical response in order to calculate the concentration of glucose in the blood sample.

However, as a result of variances in manufacturing of the test strips, calibration is needed before a particular batch of the test strips may be used with the glucose meter to obtain accurate test results. In the conventional art, the test strips are associated respective code patterns. The code patterns are normally formed by providing varying connectivities between any two contact pads provided on the test strips. The connectivities between any two contact pads will produce logic 1 or logic 0 as outputs for the glucose meter to read and to calibrate the glucose meter accordingly. As a result, the conventional glucose meter can compensate for the manufacturing variations on different batches of test strips automatically, before a user start to use the meter.

One common problem in the conventional art is the amount of coding information that can be encoded in the test strips for calibration purpose. As an example, a chip with eight pins provided within the conventional glucose meter can correspond to a test strip with eight contact pads. A common arrangement of the eight contact pads may be 2 rows of 4 contact pads at one end of any given test strip. Then, depending on the status of the electrical connectivities between one of the contact pads and a pre-defined pin, such as a ground pin, a logical value of 1 or 0 is outputted, thereby yielding a maximum of 16 codes to be used for auto-calibration purpose. Such limitation hinders the optimal use of the glucose meter and test strips.

Therefore, what is needed is a method of improving the number of auto-calibration codes that may be carried in the test strip without changing the existing structure and configuration of the glucose meter and the test strip and device for same.

SUMMARY OF THE INVENTION

In light of the drawbacks of the current art, one aspect of the present invention is to provide a biological measuring device with auto coding capabilities. In accordance with one embodiment of the present invention, the biological measuring device with auto coding capabilities may include a test strip associated with a code pattern; and a code reader electrically coupled to the test strip to read the code pattern, wherein the code reader is configured to read an output from the code pattern consisted of a first logical value, a second logical value, and a third logical value.

Another aspect of the present invention is to provide a biological measuring device adapted for use with a test strip. In one embodiment of the present invention, the test strip may be associated with a code pattern formed by a plurality of contact pads on the test strip with varying electrical connectivities between any one of the plurality of contact pads and a first or second pin pre-defined to a respective one of the plurality of contact pads, wherein the first pin is constantly set at a low voltage level, and the second pin is constantly set at a high voltage level. In accordance with the present invention, the device may include a code reader electrically coupled to the test strip to read the code pattern, wherein the code reader is configured to read an output from the code pattern consisted of a first logical value, a second logical value, and a third logical value.

Yet another aspect of the present invention is to provide a test strip adapted for use with a biological measuring device. The biological measuring device of the present invention may include a code reader. The test strip of the present invention may include a substrate; a reaction region formed by a working electrode and a reference electrode provided on said substrate at one end, said reaction region is applied with an enzyme so that an electrical response is generated when said enzyme and a test sample form a chemical reaction, and a plurality of contact pads provided on the substrate at the other end, the plurality of contact pads forming a code pattern to be read by the code reader, wherein a first pin constantly set at a high voltage level is pre-defined to one of the plurality of contact pads, wherein a second pin constantly set at a low voltage level is pre-defined to another one of the plurality of contact pads, and wherein the code pattern is formed by having varying electrical connectivities between any one of the plurality of contact pads and the first or second pin.

Yet another aspect of the present invention is to provide a method of reading a code pattern associated with a test strip adapted for use with a biological measuring device. In accordance with the present invention, the code pattern may be formed by a plurality of contact pads provided on the test strip. The biological measuring device of the present invention may have a code reader provided therein. The method of the present invention may include inserting the test strip into the code reader; reading a first logical value outputted from one of the plurality of contact pads at a first voltage level with a first strength; reading a second logical value outputted from the same contact pad at a second voltage level with a second strength, wherein the second voltage level is different from the first voltage level; outputting a third logical value if the first logical value is different from the second logical value; repeating the above steps for a predetermined number of contact pads from the plurality of contact pads; and obtaining a combined output for the code pattern associated with the test strip.

DETAILED DESCRIPTION OF THE INVENTION

Reference will now be made in detail to the embodiments of the present invention. Examples of embodiments are illustrated in the accompanying drawings, wherein like reference numbers refer to like elements throughout the specification.

The present invention discloses methods of improving coding information associated with a test strip adapted for use with a biological measuring device as well as devices and test strips for same. In accordance with one embodiment of the present invention, the biological measuring device may be configured to read an output from a code pattern associated with the test strip. In accordance with the present invention, the output from the code pattern may be consisted of a first logical value, a second logical value and a third logical value. That is, in addition to the conventional outputs of logic 1 and logic 0, the code pattern of the present invention may output a logic 2. Additionally, in accordance with one embodiment of the present invention, the biological measuring device may be configured to read logic 0, logic 1 and logic 2 from the code pattern associated with the test strip. As such, the biological measuring device of the present invention may read a greater amount of coding information in, for example, different combinations of logic 0, logic 1 and logic 2 for auto-calibration purpose.

Figure 1:
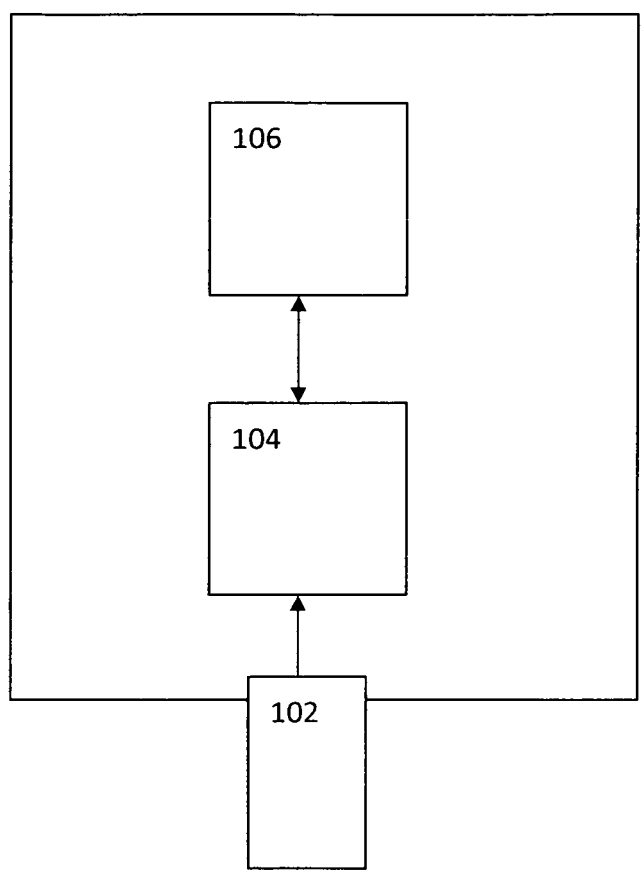
FIG. 1 illustrates a block diagram of an exemplary biological measuring device in accordance with one embodiment of the present invention.

Refer now to FIG. 1. FIG. 1 illustrates a block diagram of an exemplary biological measuring device in accordance with one embodiment of the present invention. As an example, the biological measuring device of the present invention may be a blood glucose meter capable of measuring glucose from a blood sample. However, the biological measuring device of the present invention is not limited to the blood glucose meter. Instead, any device capable of measuring a medical analyte in an individual's body fluid sample is within the scope of the present invention.

As shown in FIG. 1, the biological measuring device of the present invention may include a code reader 104 and a memory 106 provided within the biological measuring device 100. Additionally, a test strip 102 may be inserted into the biological measuring device 100 to be electrically coupled to the code reader 104 when in use. In one embodiment of the present invention, the code reader 104 may include a plurality of metal pins to be electrically coupled to the test strip 102 when in operation so as to read information, such as a code pattern, from the test strip 102.

Furthermore, the code reader 104 of the present invention may be electrically coupled to the memory 106 so that information gathered from the test strip 102 by the code reader 104 may be stored in the memory 106. Additionally, the code reader 104 of the present invention may retrieve information from the memory 106 to work with the information collected from the test strip 102.

Although FIG. 1 shows the biological measuring device 100 consisted only of the test strip 102, the code reader 104, and the memory 106, those skilled in the art would understand that the biological measuring device 100 of the present invention is not limited to these elements. For example, the biological measuring device 100 of the present invention may include a display, a plurality of buttons, a communication interface, etc., the detailed structures of which are not explained herein to prevent obscuring the focus of the present invention.

Figure 2:
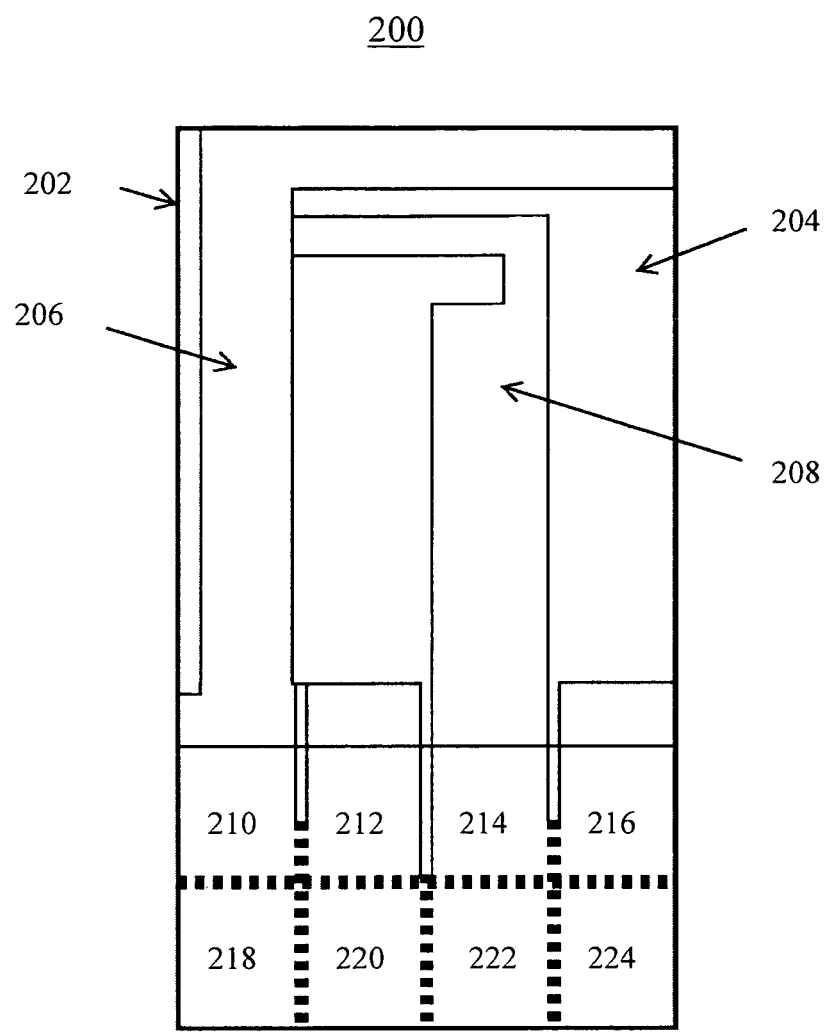
FIG. 2 illustrates a schematic diagram of an exemplary test strip in accordance with one embodiment of the present invention.

Refer to FIG. 2, which illustrates a schematic diagram of an exemplary test strip in accordance with the present invention. In accordance with one embodiment of the present invention, the test strip 200 may include a substrate 202. The substrate 202 of the present invention may be made of an insulating material, such as polyethylene terephthalate (PET) or the like. In accordance with one embodiment of the present invention, a working electrode 206 and a reference electrode 204 may be provided on the substrate 202. The working electrode 206 and the reference electrode 204 may be made of a metal material, such as silver, to form a reaction region at one end of the substrate 202. In accordance with the present invention, the reaction region may be applied with an enzyme so that when a test sample performs a chemical reaction with the enzyme at the reaction region, an electrical response may be generated from the test strip 200. In accordance with one embodiment of the present invention, a counter electrode 208 may further be provided on the substrate 202 to help balance the reaction occurring at the working electrode, among other functions known to those ordinarily skilled in the art.

In one embodiment of the present invention, the other end of the substrate 202 may be provided with a plurality of contact pads. As shown in FIG. 2, the substrate 202 may be provided with eight contact pads 210, 212, 214, 216, 218, 220, 222 and 224 at the bottom end. In accordance with the present invention, any one of the contact pads 210, 212, 214, 216, 218, 220, 222 and 224 on the test strip may be electrically couple to the code reader, such as code reader 104 of FIG. 1, to transmit electrical response.

As can be seen from FIG. 2, the contact pads of the present invention may be arranged in two rows at one end of the test strip; however, those skilled in the art would understand that any shape or arrangement of the contact pads is within the scope of the present invention. Furthermore, in accordance with the present invention, the contact pads may be physically or electrically disconnected from one another so as to produce different connectivities among the contact pads. The varying connectivities among the contact pads may, in turn, be used to read the code pattern associated with the test strip of the present invention. In accordance with the present invention, outputs read by the code reader from the code pattern may be used for auto-calibration purpose.

Figure 3:
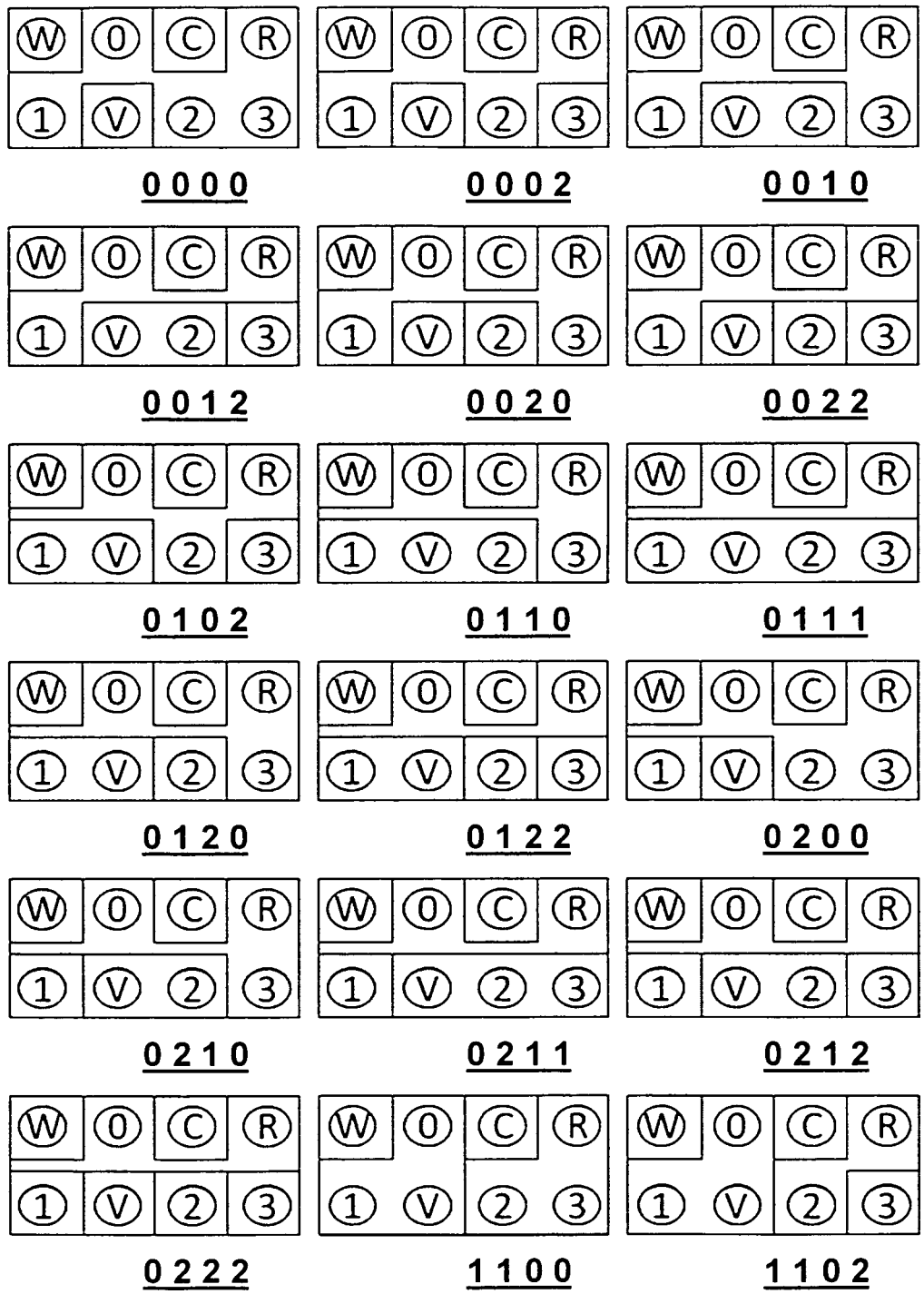
FIG. 3 illustrates schematic diagrams of exemplary code patterns in accordance with the embodiments of the present invention.

Refer now to FIG. 3, which illustrates schematic diagrams of exemplary code patterns in accordance with the various embodiments of the present invention. In accordance with one embodiment of the present invention, the working electrode (W) and the counter electrode (C) may be assigned to a respective contact pad provided on the test strip to sense the electrical response generated by the sample's reaction, as shown in FIG. 3. Those skilled in the art should know that W and C may be assigned to any contact pads provided on the test strip and are not limited to the specific contact pads as shown. Those skilled in the art should also know that the present invention is not limited to using only W and C to designate the contact pads for working and counter electrodes; instead, other designations may also be used and are within the scope of the present invention.

In accordance with one embodiment of the preset invention, one of the remaining contact pads may be pre-defined in a way such that it is constantly set at a low voltage level. As shown in FIG. 3, for example, a first pin labeled R may be pre-defined at one of the contact pads so that the voltage level is constantly set low. As such, any of the remaining contact pads that is electrically connected to R will be driven to the same Low voltage level, such as at ground.

In accordance with one embodiment of the present invention, the strength of the low voltage level pre-defined at R may be set strong enough that the voltage level of any contact pad that is electrically connected to R will not be influenced or driven up when a weaker strength of a Low or High voltage is applied to that particular contact pad. In other words, the voltage level of the contact pad that is electrically connected to R will remain at the same Low voltage level as R.

In accordance with another embodiment of the present invention, one of the contact pads on the test strip may further be pre-defined in a way such that it is constantly set at a high voltage level. As shown in FIG. 3, for example, a second pin labeled V may be pre-defined at one of the contact pads so that the voltage level is constantly set high. As a result, any of the remaining contact pads that is electrically connected to V will be driven to the same High voltage level.

In accordance with one embodiment of the present invention, the strength of the high voltage level pre-defined at V may be set strong enough that the voltage level of any contact pad that is electrically connected to V will not be influenced or driven down when a weaker strength of a Low or High voltage is applied to that particular contact pad. In other words, the voltage level of the contact pad that is electrically connected to V will remain at the same High voltage level as V.

In yet another embodiment of the present invention, bits 0, 1, 2 and 3 may be further assigned to a respective remaining contact pad on the test strip. In one embodiment of the present invention, a logical value may be outputted from each contact pad depending on its electrical connectivity to either R or V. For example, if bit 0 is electrically connected to R, then the voltage level at bit 0 will be driven to the same Low level as R, and a logic 0 may be outputted to represent such low voltage. Alternatively, if bit 0 is electrically connected to V, then the voltage level at bit 0 will be driven to the same High level as V, and a logic 1 may be outputted to represent such high voltage.

Furthermore, in accordance with one embodiment of the present invention, a weaker strength of the high voltage level and that of the low voltage level may also be applied to bit 0 in a predetermined time frame, such as within 5 seconds, to detect whether a voltage change occurs at the particular contact pad. For example, if bit 0 is electrically isolated from either R or V, it will not be driven to the corresponding Low or High voltage level when a weaker strength of the high voltage or a weaker strength of the low voltage is applied to the contact pad. Instead, the voltage level at bit 0 will change as the weaker strength of the voltage is applied. That is, bit 0 is in a high impedance state, Hi-Z. In such an embodiment, bit 0 may output a logic 0 when the weaker strength of the low voltage is applied and output a logic 1 when the weaker strength of the high voltage is applied. That is, when bit 0 is in the high impedance state, the output of bit 0 changes as the voltage level applied thereto changes.

In accordance with the present invention, the code reader may recognize the different logical values outputted from the same contact pad within a predetermined time frame and read out a logic 2 to represent such a change. As such, by pre-defining one of the contact pads with a pin that is constantly set at a high voltage, in addition to pre-defining another one of the contact pads with a pin that is constantly set at a low voltage, the code pattern associated with the test strip of the present invention may create a third output state, which would change its logic output as the voltage applied thereto changes, thereby increasing the possible combinations of the logical values outputted from each contact pad.

Take the test strip on the top left corner of FIG. 3 as an example. The test strip of the present invention may pre-define W, C, V and R as shown. As explained earlier, W and C may be connected to the working and counter electrodes to sense the electrical response. Additionally, V and R may be pre-defined to be constantly set at a high voltage level and a low voltage level, respectively. Furthermore, the test strip of the present invention may be manufactured such that bits 0, 1, 2 and 3 are further assigned to a respective remaining contact pad. However, those skilled in the art should know that W, C, V, R and bits 0-3 may be assigned to different contact pads on the test strip, and such assignments are still within the scope of the present invention.

In this example, bit 0 is electrically connected to R. In other words, the voltage level at bit 0 is driven to the same Low voltage as R. Bit 1 as well as bit 2 and bit 3 are also electrically connected to R. That is, the voltage levels at bits 1, 2 and 3 are also driven to the same Low voltage as R. As a result, the output given at each contact pad is 0. That is, the code reader of the present invention may read out a combined output of 0000 for this particular code pattern associated with the test strip.

Take the left code pattern in the second row in FIG. 3 as another example. In this case, bits 0 and 1 are both electrically connected to R, and thus output logic 0. Bit 2, on the other hand, is electrically connected to V. As such, the voltage level at bit 2 is drive to the same High voltage as V and thus outputs logic 1. Bit 3, different from the other bits, is electrically isolated from R and V, and thus when a weaker strength of the High voltage is applied to bit 3, the voltage level will be influenced and driven to the high voltage but with the weaker strength. Additionally, when a weaker strength of the Low voltage is applied at bit 3, the voltage level will again be influenced and changed accordingly. As such, bit 3 will output a logic 1 when the weaker strength of the High voltage is applied and a logic 0 when the weaker strength of the Low voltage is applied.

In accordance with the present invention, the code reader may be configured to record the output changes within a predetermined time frame, and read out a logic 2 to reflect such change. As such, the code reader may read out a combined output of 0012 from the code pattern associated with the test strip.

In accordance with one embodiment of the present invention, the weaker strength of the high voltage level applied to bit 3 in the previous example is not necessarily the same as the weaker strength of the low voltage level applied to bit 3. In other words, as long as the strength applied is capable of manipulating and thus changing the voltage level at bit 3 it is within the scope of the present invention.

Figure 4:
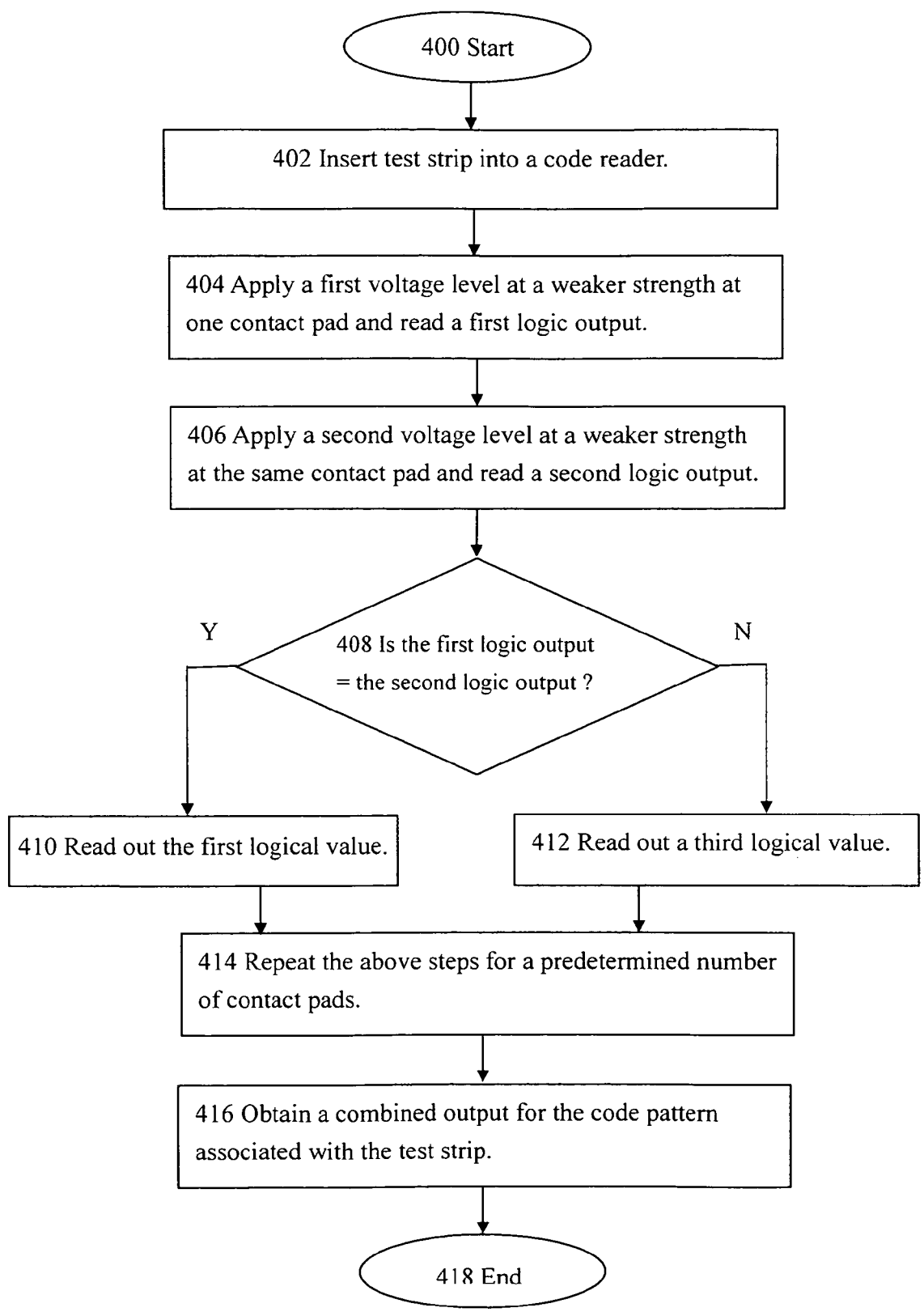
FIG. 4 illustrates a flow chart of an exemplary method of reading a code pattern associated with a test strip adapted for use with a biological measuring device in accordance with one embodiment of the present invention.

Refer to FIG. 4, which illustrates a flow chart of an exemplary method of determining coding information associated with a test strip adapted for use with a biological measuring device in accordance with one embodiment of the present invention. As shown in FIG. 4, the method starts at step 400. At step 402, the present method may insert a test strip, such as the test strip 102 of FIG. 1, into a code reader, such as the code reader 104 of FIG. 1, provided in a biological measuring device. As mentioned above, the biological measuring device of the present invention may be a blood glucose meter capable of measuring glucose from a blood sample. However, the biological measuring device of the present invention is not limited to the blood glucose meter. Instead, any device capable of measuring a medical analyte in an individual's body fluid sample is within the scope of the present invention.

Then, at step 404, a first voltage level at a weaker strength may be applied to one of the contact pad, and the first logic output is read. In one embodiment of the present invention, the weaker strength of the first voltage level may be in comparison to the High voltage level at, for example, V. As such, the voltage level at a contact pad that is electrically connected to V will not change, whereas the voltage level at the same contact pad that is electrically isolated from V will be influenced.

At step 406, a second voltage level at a weaker strength is applied to the same contact pad, and the second logic output is read. In one embodiment of the present invention, the weaker strength of the second voltage level may be in comparison to the Low voltage level at, for example, R. As such, the voltage level at a contact pad that is electrically connected to R will not change, whereas the voltage level at the same contact pad that is electrically isolated from R will be influenced.

Then, at step 408, the code reader of the present invention may determine whether the first logic output is the same as the second logic output. If so, it is an indication that the contact pad is electrically connected to either R or V and thus is driven by the Low or High voltage at all time. As a result, at step 410, the code reader of the present invention may read out the first logical value, such as logic 0, if it is at Low voltage, or logic 1, if it is at High voltage.

On the other hand, if the first logic output is not the same as the second logic output, then it is an indication that the contact pad is electrically isolated from V and R, and thus the voltage level at such contact pad will change as the voltage applied thereto changes. As a result, at step 412, the code reader of the present invention may read out a third logical value, such as logic 2, to represent the change.

In accordance with the present invention, the method may repeat the above steps for a predetermined number of contact pads, such as for bits 0, 1, 2 and 3, at step 414. As a result, the code reader may obtain a combined output for the code pattern associated with the test strip at step 416. The method of the present invention may end at step 418.

Optionally, the present invention may pre-define a first pin to be constantly set at the first voltage level with a stronger strength at one of the contact pads so that any other one of the contact pads that is electrically connected to the first pin is driven to the first voltage level. For example, a first pin, R, may be constantly set at the Low voltage level, such as ground, with a stronger strength at one of the contact pads so that any other one of the contact pads that is electrically connected to R is driven to the Low voltage and remains Low when a weaker strength of the Low or High voltage is applied thereto.

Additionally, the present invention may pre-define a second pin to be constantly set at the second voltage level with a stronger strength at another one of the contact pads so that any other one of the contact pads that is electrically connected to the second pin is driven to the same second voltage level. For example, a second pin, V, may be constantly set at the High voltage level with a stronger strength at one of the contact pads so that any other one of the contact pads that is electrically connected to V is driven to the High voltage and remains High when a weaker strength of the Low or High voltage is applied thereto.

Also, in accordance with the present invention, the biological measuring device of the present invention may store the first logical value and the second logical value in a memory provided therein, such as memory 106 in FIG. 1. Furthermore, in accordance with the present invention, the biological measuring device of the present invention may store the third logical value in the memory provided therein, such as memory 106 in FIG. 1. Additionally, in accordance with the present invention, the biological measuring device of the present invention may store the combined output obtained by the code reader in the memory for future reference.

In accordance with the present invention, the code reader's capability to read the code pattern associated with the test strip with increased combination outputs increases the amount of information that may be encoded on the test strip without changing the existing structure and configuration of the biological measuring device and the test strip.

While the invention has been described in conjunction with exemplary preferred embodiments, it is to be understood that many alternatives, modifications, and variations will be apparent to those skilled in the art in light of the foregoing description. Accordingly, the present invention embraces all such alternatives, modifications, and variations. All matters set forth herein or shown in the accompanying drawings are to be interpreted in an illustrative and non-limiting sense.

What is claimed is:

1. A biological measuring device with auto coding capabilities, said device comprising:
    a test strip associated with a code pattern, said code pattern having a first contact pad, a second contact pad and a third contact pad; and
    a code reader electrically coupled to said test strip to read said code pattern, said code reader having a first pin containing a first voltage level applied by said code reader, a second pin containing a second voltage level applied by said code reader, and a third pin containing a third voltage level applied by said code reader,
    wherein said first pin constantly contacts said first contact pad so as to allow said code reader to read an existence of said first voltage level by said third pin,
    wherein said second pin constantly contacts said second contact pad so as to allow said code reader to read an existence of said second voltage level by said third pin,
    wherein said third pin constantly contacts said third contact pad so as to receive a voltage response, and
    wherein said voltage response is said first voltage level, said second voltage level, or said third voltage level.

2. The device of claim 1, wherein said third voltage level is a weaker strength of said first or second voltage level.

3. The device of claim 1, wherein said third contact pad is selectively driven to said first voltage level or said second voltage level depending on its electrical connection to said first and second contact pads.

4. The device of claim 1, wherein said code reader further applies a weaker strength of said first voltage level and a weaker strength of said second voltage level separately to said third pin and reads two response voltage levels from said third contact pad so as to identify its electrical connection to said first and second contact pads.

5. The device of claim 4, wherein said code reader reads out a first logical value and a second logical value from said third contact pad, and wherein said first logical value is different from said second logical value.

6. The device of claim 5, wherein said code reader reads out a third logical value from said third contact pad having a voltage change.

7. The device of claim 6, wherein said third logical value occurs in a high impedance state.

8. The device of claim 1, wherein said first voltage level is a HIGH voltage.

9. The device of claim 1, wherein said second voltage level is a LOW voltage.

* * * * *